United States Patent [19]
Devlin et al.

[11] Patent Number: 5,813,404
[45] Date of Patent: Sep. 29, 1998

[54] ELECTRODE CONNECTOR SYSTEM

[75] Inventors: Philip H. Devlin, Brookline; Nassib G. Chamoun, West Roxbury; John R. Shambroom, Arlington; Mark E. Bruckner, Reading; Todd A. Marcus, Groton, all of Mass.

[73] Assignee: Aspect Medical Systems, Inc., Natick, Mass.

[21] Appl. No.: 545,981

[22] Filed: Oct. 20, 1995

[51] Int. Cl.⁶ ............................................ A61B 5/04
[52] U.S. Cl. ........................................... 128/639
[58] Field of Search ....................... 128/660.01, 639, 128/731–733, 630

[56] References Cited

U.S. PATENT DOCUMENTS

| | | | |
|---|---|---|---|
| 3,380,445 | 4/1968 | Frasier | 128/2.06 |
| 3,572,322 | 3/1971 | Wade | 128/2.06 |
| 4,072,145 | 2/1978 | Silva | 128/2.1 E |
| 4,311,152 | 1/1982 | Modes et al. | 128/641 |
| 4,353,372 | 10/1982 | Ayer | 128/640 |
| 4,557,271 | 12/1985 | Stoller et al. | 128/734 |
| 4,595,013 | 6/1986 | Jones et al. | 128/644 |
| 4,638,807 | 1/1987 | Ryder | 128/644 |
| 4,695,955 | 9/1987 | Falsondier | 364/413 |
| 4,706,679 | 11/1987 | Schmidt et al. | 128/639 |
| 4,768,496 | 9/1988 | Kreizman et al. | 128/24 A |
| 4,770,180 | 9/1988 | Schmidt et al. | 128/644 |
| 4,852,572 | 8/1989 | Nakahashi et al. | 128/640 |
| 4,928,696 | 5/1990 | Henderson et al. | 128/644 |
| 4,957,109 | 9/1990 | Groeger et al. | 128/640 |
| 5,209,235 | 5/1993 | Brisken et al. | 128/662.06 |
| 5,246,003 | 9/1993 | DeLonzor | 128/633 |
| 5,251,631 | 10/1993 | Tsuchiko et al. | 128/661.01 |
| 5,305,746 | 4/1994 | Fendrock | 128/641 |
| 5,387,122 | 2/1995 | Goldberger et al. | 439/353 |

FOREIGN PATENT DOCUMENTS

| | | |
|---|---|---|
| 0070674 | 1/1983 | European Pat. Off. . |
| 0132380 | 1/1985 | European Pat. Off. . |
| 026652 | 5/1988 | European Pat. Off. . |
| 4339049 | 5/1995 | Germany . |
| 2075194 | 11/1981 | United Kingdom . |

*Primary Examiner*—Francis Jaworski
*Attorney, Agent, or Firm*—Hale and Dorr LLP

[57] ABSTRACT

Disclosed is a physiological electrical signal connector system which one connector connected to an electrode set and another connector connected to a digital signal convertor which leads to a patient monitor. Each type of electrode set has a specific code identified with it and when connected to the digital signal convertor, the connector code is recognized by the digital signal convertor. The connector code is then relayed to the monitor which will self-configure based on the identified code.

14 Claims, 5 Drawing Sheets

5,813,404

ELECTRODE CONNECTOR SYSTEM

BACKGROUND OF THE INVENTION

This invention relates to physiological electrical signal monitors and more particularly to a connector system used to connect electrodes to such monitors.

Monitors which detect and analyze physiological electrical signals, such as EEG, EKG and EMG signals, are being used for an increasing number of different purposes. For example, an EEG monitor which processes EEG signals in a manner described in U.S. Pat. Nos. 4,907,597; 5,010,891 and 5,320,109 issued to Chamoun, et al., is being used to determine a depth of anesthesia of a patient.

The medical personnel utilizing EEG monitors for purposes such as determining depth of anesthesia are not as sophisticated as the personnel which traditionally use EEG monitors for analyzing EEG signals. Operators monitoring depth of anaesthesia are often not doctors trained in neurology and are not as skilled and knowledgable concerning the proper placement of the electrodes which acquire the EEG signals from the brain. Such proper placement is further complicated by the fact that with different types of monitoring, signals from different portions of the brain are required. For example, two channel bipolar signal values are required for isolating the hemipheres of the brain, while two channel referential signal values would be required for referencing to a common point on the brain for monitoring the effects of anesthetics on the brain. Since the placement of the electrodes is extremely important to obtain proper readings, the electrodes must be placed in the appropriate locations and the appropriate type and number of electrodes must actually be used. Because the same monitor may be used to take several different modes of monitoring, electrodes must be placed in different locations and the number of required electrodes is different for different modes of monitoring.

In U.S. Pat. No. 5,265,607 which was issued to Moberg, a patient-monitoring electrode connection apparatus is described in which configuration cards are used in a data acquisition module. The problem with such a system is that the operator must not only use appropriate electrode cables and connect the electrodes properly but must also insert the appropriate configuration card. This raises the additional possibility of human error which may result if an inappropriate card is selected.

It is therefore a principal object of the present invention to provide a cable interface system which will enable a physiological electrical signal monitor to determine the type of electrode system being attached to the monitor.

It is another object of the present invention to allow physiological electrical signal monitor connector to make use of different types and numbers of electrode configurations.

A further object of the present invention is to provide an easy to use electrode-to-monitor cable connector system which is moisture resistant and includes an integral key structure which prevents connection of incompatible connectors.

SUMMARY OF THE INVENTION

The physiological electrical signal connector system of the present invention utilizes one connector connected to an electrode set and another connector connected to a digital signal convertor which leads to a patient monitor. Each type of electrode set has a specific code identified with it and when connected to the digital signal convertor, the connector code is recognized by the digital signal convertor. The connector code is then relayed to the monitor which will self-configure based on the identified code.

These and other objects are features of the present invention and will become more fully understood from the following detailed description which should be read in light of the accompanying drawings in which corresponding reference numerals refer to corresponding parts throughout the several views.

DETAILED DESCRIPTION OF PREFERRED EMBODIMENTS

Figure 1:
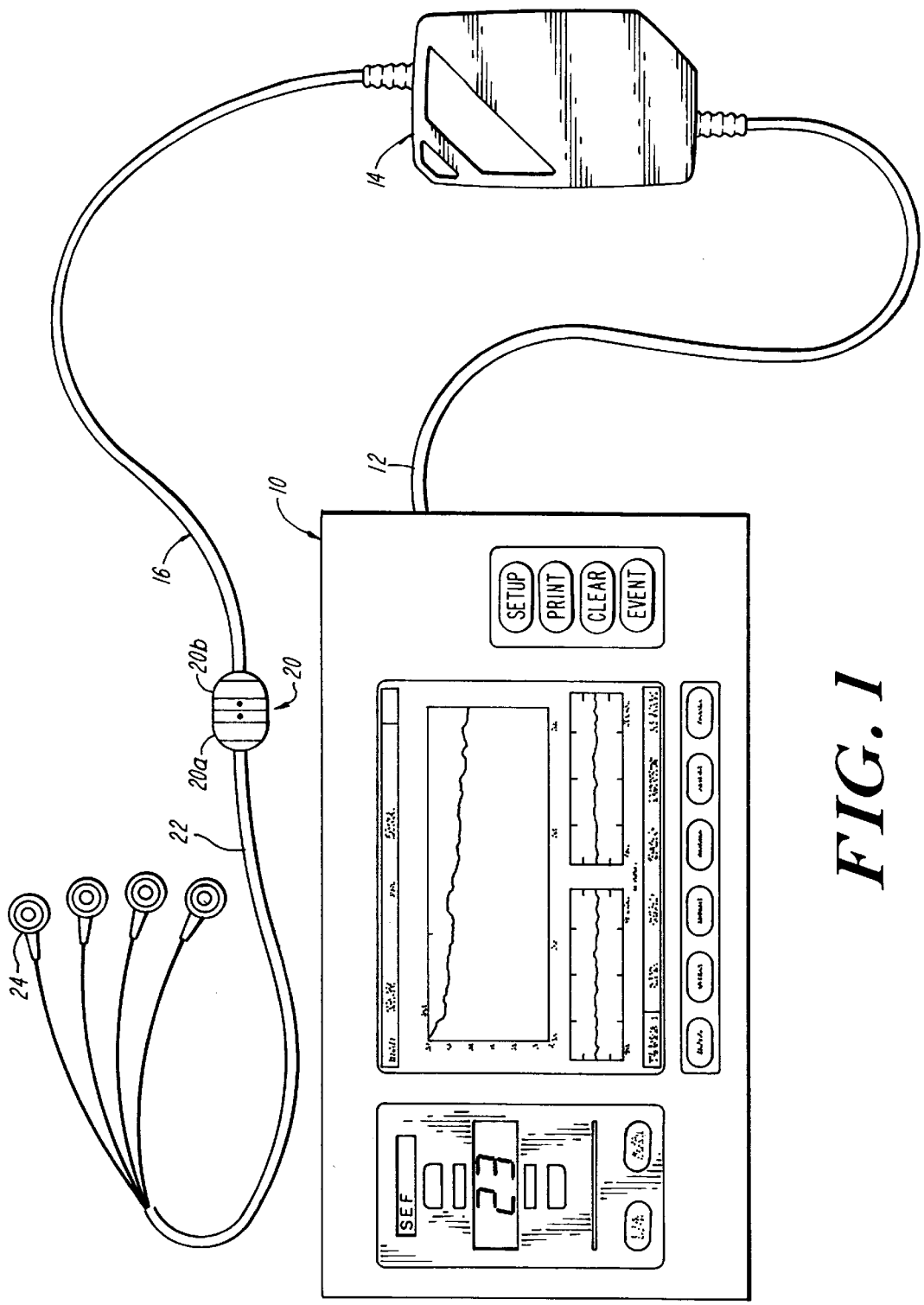
FIG. 1 is a diagram of the components of a physiological electrical signal monitor utilizing the electrode connector system of the present invention.

Referring first to FIG. 1, a physiological electrical signal monitor such as an EEG monitor receives digital physiological electrical signals, such as EEG signals, through a monitor interface cable 12. Monitor interface cable 12 is connected to a digital signal convertor 14 which, in the embodiment shown, is used to acquire analog physiological electrical signals from the electrodes 24 and to convert such analog signals to digital signals. Such a digital signal convertor is described in U.S. Pat. Nos. 5,368,041 and 5,381,804 the teachings of which are incorporated herein by reference. A pigtail (or short) cable 16 is connected to the digital signal convertor 14 to deliver analog signals from the electrodes to the digital signal converter 14. The pigtail cable 16 is attached to a two piece interface connector 20 which includes female and male parts 20a, 20b. In other embodiments, the digital signal convertor 14 may be incorporated in the monitor 10 in which case the pigtail cable 16 is connected directly from male part 20b to the monitor 10. In still other embodiments the digital signal converter 14 may be positioned between the female part 20a and the electrodes 24 either in line in PIC 22 or as attached to electrodes 24. Connected to the interface connector 20 is a patient information cable or PIC 22 which leads from the electrode snap connectors 24 which, in the case of an EEG monitor, are attached to disposable electrodes placed on the head of a patient. The PIC 22 could also be attached directly to electrodes which are placed directly on the patient's head. The term "electrode" will be used in this specification to refer to either an electrode placed directly on a patient's head or to a snap connector. Where a monitor is used for other purposes (such as EKG) the electrodes are connected to a portion of the body which will deliver the appropriate signals.

Figure 2A:
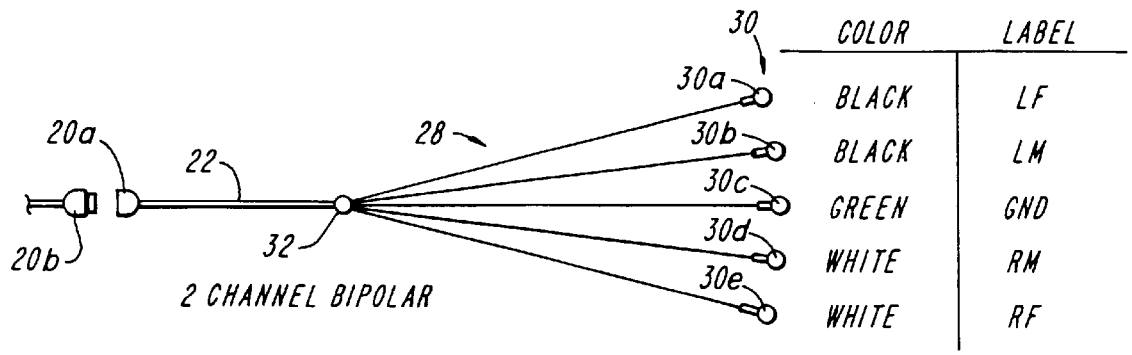
FIGS. 2a–2c are diagrams of examples of various electrode set configurations utilized in the system of FIG. 1.
Figure 2B:
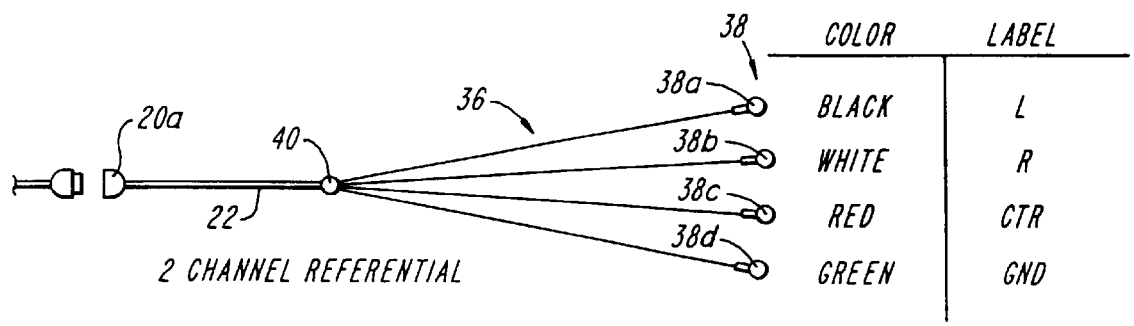
Figure 2C:
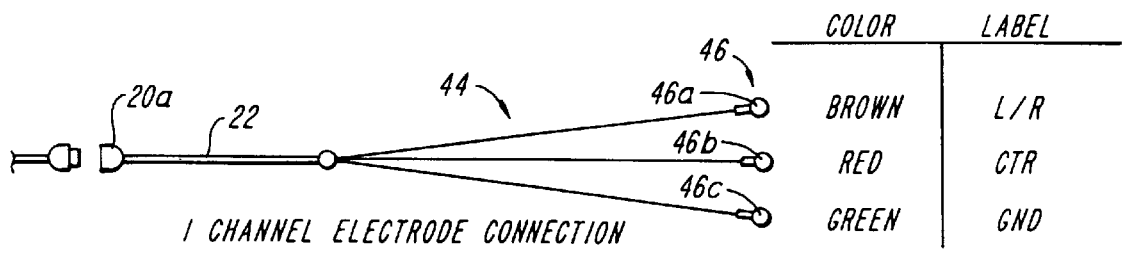
Figure 3A:
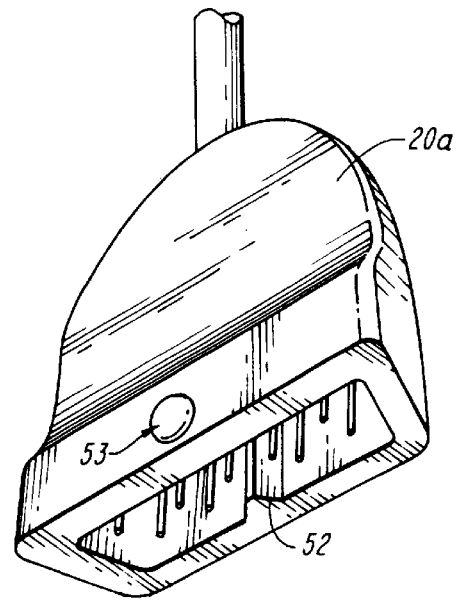
FIGS. 3a–3b are perspective views showing the two components of the connector system shown in FIG. 1.
Figure 3B:
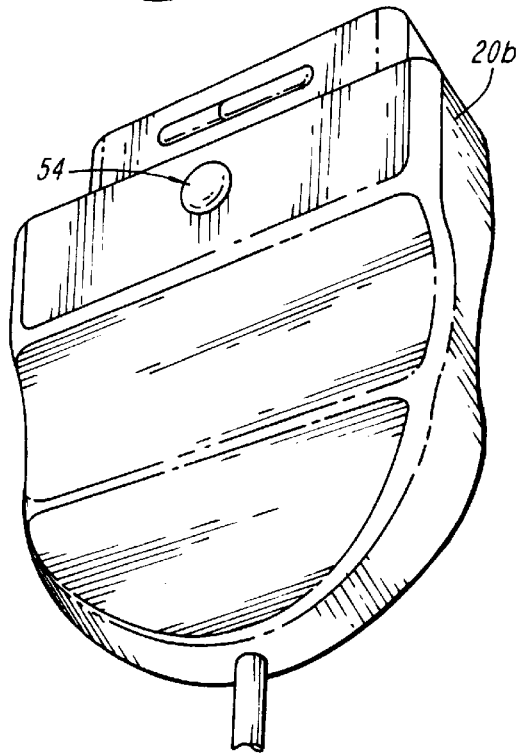
Figure 4A:
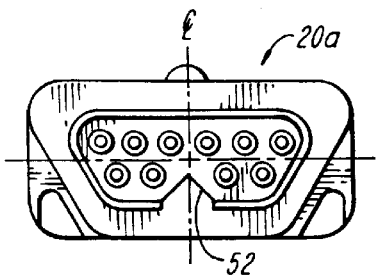
FIGS. 4a–4b are representative views of the socket and pin configuration of the connector system of the present invention shown in FIG. 3 (such views, however, are not representations of the respective dimensions of the connector components)
Figure 4B:
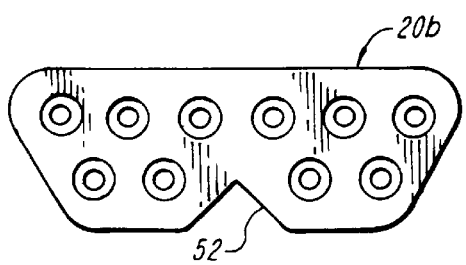

Referring now to FIGS. 2a–2c, three examples of different electrode sets are shown that can be used with monitor 10. In FIG. 2a, electrode set 28 is a two channel bipolar electrode set having five individual electrodes 30. The electrodes 30 are color coded and labeled. In one embodiment, electrode 30a and electrode 30b are color coded black with electrode 30a being used to acquire signals from the left frontal region and electrode 30b acquiring signals from the left mastoid region. Electrode 30c which is connected to ground is color coded in green. Electrodes 30d and 30e are color coded as white with electrode 30d used to acquire signals from the right mastoid region and electrode 30e acquiring signals from the right frontal region.

A two channel referential electrode system 36 includes four color coded electrodes 38. Electrode 38a which is color coded black is connected to the left forehead region. Electrode 38b which is white color coded is connected to the right forehead region. Electrode 38c which is color coded red is connected in the center of the forehead and electrode 38d which is color coded green is connected to ground.

A one channel electrode set 44 includes three electrodes 46. Electrode 46a which is color coded brown is connected to either the left or right forehead region and electrode 46b which is color coded red is connected to the center of the forehead. Electrode 46c which is color coded green is connected to ground.

In all three of the described embodiments, all ground connections are of the same color which in the embodiment described is green.

The interface connector 20 is more clearly shown in FIGS. 3a–3b and FIGS. 4a–4b. The female connector 20a includes ten pins which meet with the ten sockets of connector 20b. Both connectors 20a and 20b have a V-shaped cut region 52 which insures that only appropriate cable connectors can be mated with each other. Connectors 20a also include a circular recess 53 on its top surface and connector 20b includes a raised circular "bimp" 54. When connectors 20a and 20b are united, the recess 53 and bimp 54 provide an indication of the appropriate orientation of connectors 20a, 20b and bimp 54 sits in recess 53 to help lock connectors 20a and 20b.

Of the 10 pins and sockets, one pin and one socket is a ground connection, four each of the pins and sockets are signaling information lines and four each of the pins and sockets are used to identify the appropriate electrode set being connected. In the embodiment shown the tenth pin and socket is not used. The unused pin and socket could be used in other embodiments to recognize a greater number of electrode sets or to supply an additional information line to the monitor.

The PIC 22 is a reusable cable that transitions from the pigtail cable 16 to the electrode 24. The PIC 22 passes the EEG signals from the electrodes on the subject's head through the pigtail cable 16 to the digital signal convertor 14 for analog to digital conversion. A unique PIC type identifying code is incorporated into the cable connector 20a for each type of PIC 22. In the embodiment shown, the interface connector 20 contains four EEG (and possibly a fifth) signal lines (wires) plus four connector identification logical signal lines. The EEG signal wires transmit the analog EEG signal from sensing electrodes 24 on a patient's head to the digital signal convertor amplifier module 14. The logical connector identification signal lines are used to generate a digital code that identifies a specific type of PIC 22 and it may also identify a specific electrode array that is attached to the PIC 22 (including such information as electrode manufacture date, lot code, revision level, etc). As explained above, it is important that the PIC type is identified by the monitor 10 so that the monitor 10 can determine the number of active EEG electrodes and the electrode positions on the subject's head. In this way the monitor will auto configure for a particular EEG monitoring session.

Figure 6:
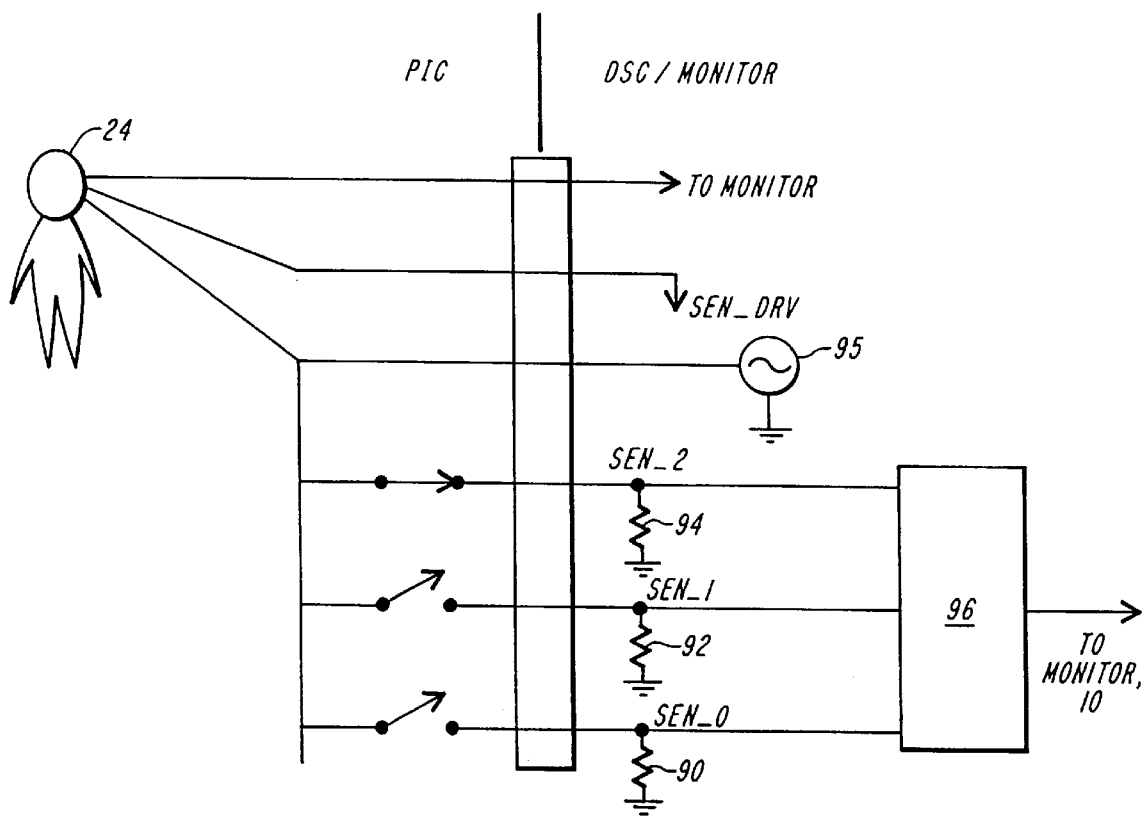
FIG. 6 is a diagram of the circuitry of the connector system of FIG. 3 which recognizes the appropriate electrode set.

For simplicity's sake, an embodiment where only three logical connector identification signal lines are utilized to identify the PIC is shown in FIG. 6 in which a three bit binary code identification scheme is used. The binary code is hard-wired in the patient interface connector 20a and the digital signal convertor 14 detects the sensor ID signal connections at the end of the pigtail cable 14. The code is set by selectively shorting a common drive signal line [SEN_DRV] to the three PIC code signal lines [SEN_0:2]. These are the three connector identification signal lines. The SEN_DRV line is pulsed (driven) to a logic high at 8,192 Hz by the pulse generator 95 located in the digital signal converter 14. Pulsing the line prevents a fault condition, such as a broken PIC connector, from injecting more than 50 micro amps of current into the patient, as required by IEC 601-1 which is the standard for Medical Equipment, published by the International Electrotechnical Commission. The frequency of the pulse is chosen to be at the Nyquist frequency of the digitizers. These pulses will not interfere with the EEG signal because at this frequency it will alias onto itself only in the first stage of decimation, and will subsequently be filtered out completely by the digital signal processor.

The patient interface connector code signal lines are pulled down to a logic "0" by resistors 90, 92, 94 located in the digital signal converter 14 at the input to the receiver circuit 96, which is a D-Flip-flop in a preferred embodiment. As the common [SEN_DRV] line is driven high by the pulse generator, the patient interface connector code lines [SEN_0:2] are then read (i.e. clocked in) by receiver circuit 96, which transmits the binary code to the monitor 10. The patient interface connector code signal lines that are shorted to the drive signal will be read as a logic "1." The patient interface connector code signal lines that are left open will be read as a logic "0." Such a coding scheme allows for eight different PIC cable types as follows:

| # | Code | Cable Type |
|---|------|------------|
| 1 | 000 | PIC not connected |
| 2 | 001 | 2 channel Bipolar (5 signal wires in use) |
| 3 | 010 | 2 channel Referential (4 signal wires in use) |
| 4 | 011 | 1 channel electrode connection |
| 5 | 100 | 1 channel sensor connection |
| 6,7,8 | | Unassigned Spares |

Figure 5:
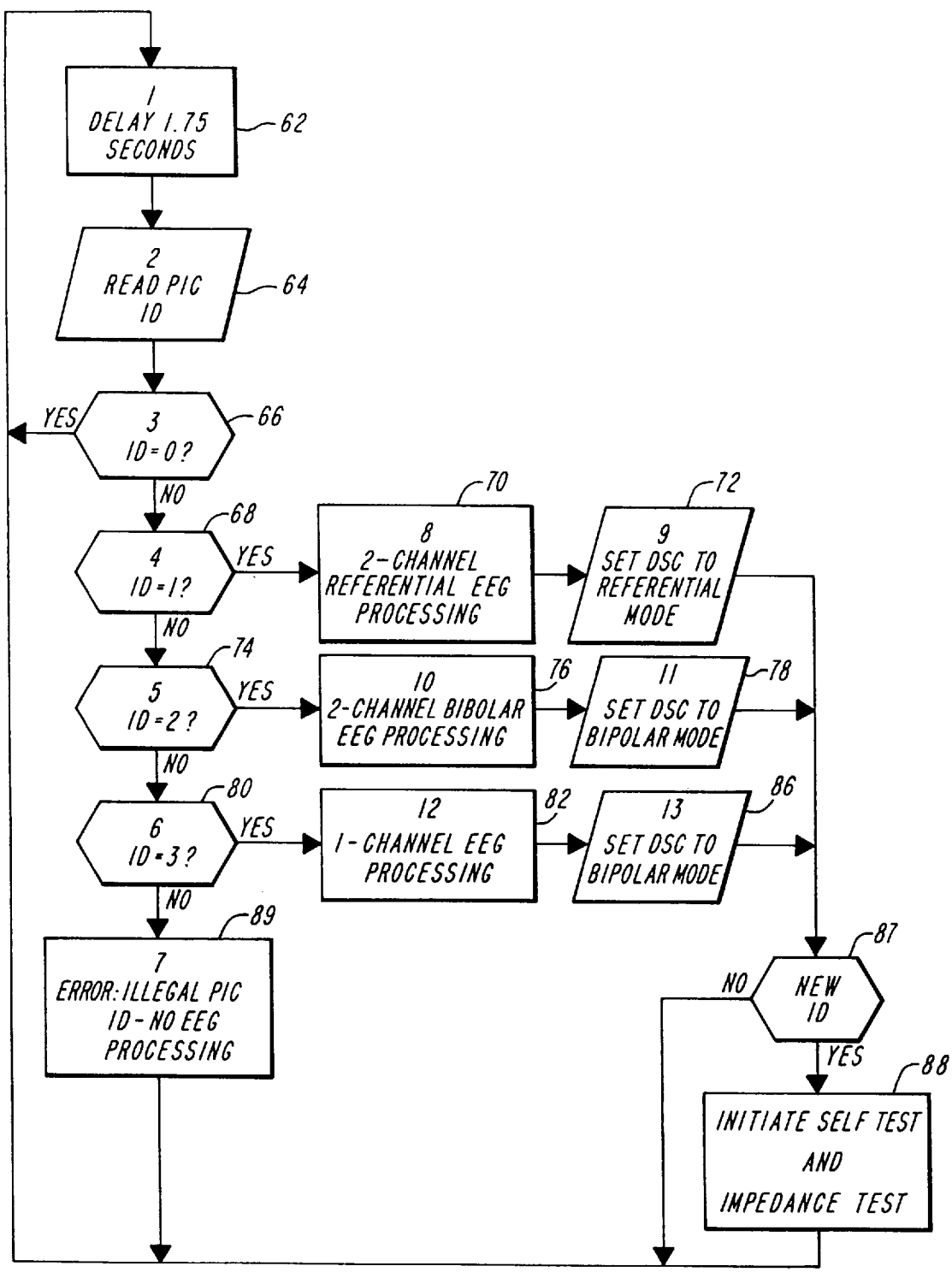
FIG. 5 is a flowchart of the steps performed by the monitor to identify the particular PIC being used by the system in FIG. 1.

Referring now to FIG. 5 the process for determining the appropriate PIC will now be described. In step 62, a CPU in the monitor 10 periodically reads the PIC code, which in a preferred embodiment is read every 1.75 seconds. In step 64 the CPU in monitor 10 reads a PIC ID in the manner described below with reference to FIG. 6. If the PIC ID is determined in step 66 to be "000," (which indicates that a PIC is not connected) the system reiterates the process after each 1.75 second delay and continues to attempt to read a new PIC ID.

If the PIC ID is determined in step 68 to be "001," a two channel referential EEG electrode set is detected and the monitor (10) is configured for 2-channel referential EEG processing in step 70. The digital signal convertor is set to referential mode in step 72. If, in step 74, the PIC ID is equal to "010," the system recognizes a two channel bipolar EEG electrode set and the monitor (10) is configured for 20 channel biopolar EEG processing in step 76. The digital signal convertor is then set in step 78 to bipolar mode.

If the PIC ID is determined in step 80 to be equal to "011," the system has detected a one channel EEG processing cable and the monitor 10 is configured for 1-channel EEG processing in step 82. In step 86, digital signal convertor is set to bipolar mode. If any other PIC ID is detected, error messages are generated and displayed in step 87 indicating that an illegal PIC ID was detected, and that no EEG processing should occur. After the CPU in monitor 10 determines that the PIC ID is valid, the monitor checks if the PIC ID is a new PIC ID. If a new PIC ID is recognized the monitor initiates a self test in step 88 followed by an electrode impedance test in step 89. After this series of steps the system again returns after a 1.75 second delay to read additional PIC IDs in step 62.

In alternate embodiments where four pins are allocated for PIC IDs, the digital signal convertor 14 can recognize up to 15 different combinations of pigtail, PIC or connector type.

While the foregoing invention has been described with reference to its preferred embodiments, various alterations and modifications will occur to those skilled in the art. All such variations and modifications are intended to fall within the scope of the appended claims.

What is claimed is:

1. An electrode connector system which is used to connect one or more electrodes to a physiological signal monitor, said connector system comprising:

an electrode connector connected through a patient interface cable to said one or more electrodes:

a monitor connector connected to a pigtail cable;

each of said electrode connector and said monitor connector having a plurality of signal lines dedicated to transmit a corresponding one or more channels of a predetermined type of physiological signals and at least two electrode connector identification lines dedicated to transmit a unique identification code associated with a unique electrode configuration.

2. The electrode connector system of claim 1 further comprising a digital signal converter for converting analog physiological signals obtained by said one or more electrodes into digital signals to be processed by said monitor, said digital signal converter being attached at one end to said pigtail cable and at a second end to a monitor interface cable.

3. The electrode connector system of claim 2 further comprising a unique identification code hardwired into said electrode connector and wherein said digital signal converter further comprises means for interpreting said hardwired code.

4. The electrode connector system of claim 1 further comprising a unique identification code hardwired into said electrode connector.

5. The electrode connector system of claim 1 wherein the monitor is connected to one end of said monitor connector.

6. The electrode connector system of claim 1 wherein said electrode connector includes a cutout region and said monitor connector includes a corresponding cutout region, whereby when said electrode connector and said monitor connector are united one of said cutout regions fits within a second of said cutout regions.

7. The electrode connector system of claim 1 further comprising a pulse generator for periodically sensing said unique identification code.

8. The electrode connector system of claim 7 wherein said pulse generator generates pulses at an analog to digital conversion Nyquist frequency.

9. The electrode connector system of claim 1 wherein the monitor further comprises a processor for processing physiological signals if said monitor recognizes a unique identification code as a supported code.

10. The electrode connector system of claim 1 wherein the monitor further comprises a processor for initiating a self test procedure if said monitor recognizes a unique identification code as a supported code.

11. The electrode connector system of claim 1 wherein the monitor further comprises a processor for initiating an electrode impedance test if said monitor recognizes a unique identification code as a supported code.

12. The electrode connector system of claim 1 wherein the monitor further comprises a processor for self-configuring the monitor to receive the number and type of electrodes identified by a unique identification code.

13. The electrode connector system of claim 1 wherein the monitor further comprises a processor for determining from said unique identification code the relative position of said one or more electrodes.

14. The electrode connector system of claim 1 wherein the monitor further comprises a processor for determining the type of said pigtail cable connected to the monitor.

* * * * *